Jan. 31, 1933. W. R. GRAY Plant Pat. 54

EVERGREEN PLANT

Filed Oct. 24, 1931

Patentee

Willis R. Gray

By Mason Fenwick & Lawrence

Attorneys

Patented Jan. 31, 1933

Plant Pat. 54

UNITED STATES PATENT OFFICE

WILLIS RUSSELL GRAY, OF OAKTON, VIRGINIA

EVERGREEN PLANT

Application filed October 24, 1931. Serial No. 570,925.

This invention relates to a new and ornamental evergreen plant belonging to the genus *Juniperus*. It is a variety of *Juniperus Communis*, nearest to *J. suecica* and *J. hibernica*, but distinguishes from these both in color of foliage and habit of growth.

The new variety is disclosed in the accompanying water color reproduction, in which Figure 1 represents a three year old plant taken from life, but on a somewhat reduced scale;

The new variety is very narrowly columnar in shape, the branches are up-right to the tips, the leaves extend nearly at right angles to the branches and branchlets, and are stiff. The stiffness of the leaves and their approximate perpendicular disposition of growth gives to the plant a prickly feel, when laterally touched. This characteristic so distinguishes the new plant that it can be readily identified from *J. suecica* and *J. hibernica* by a blindfold test.

Figure 1:
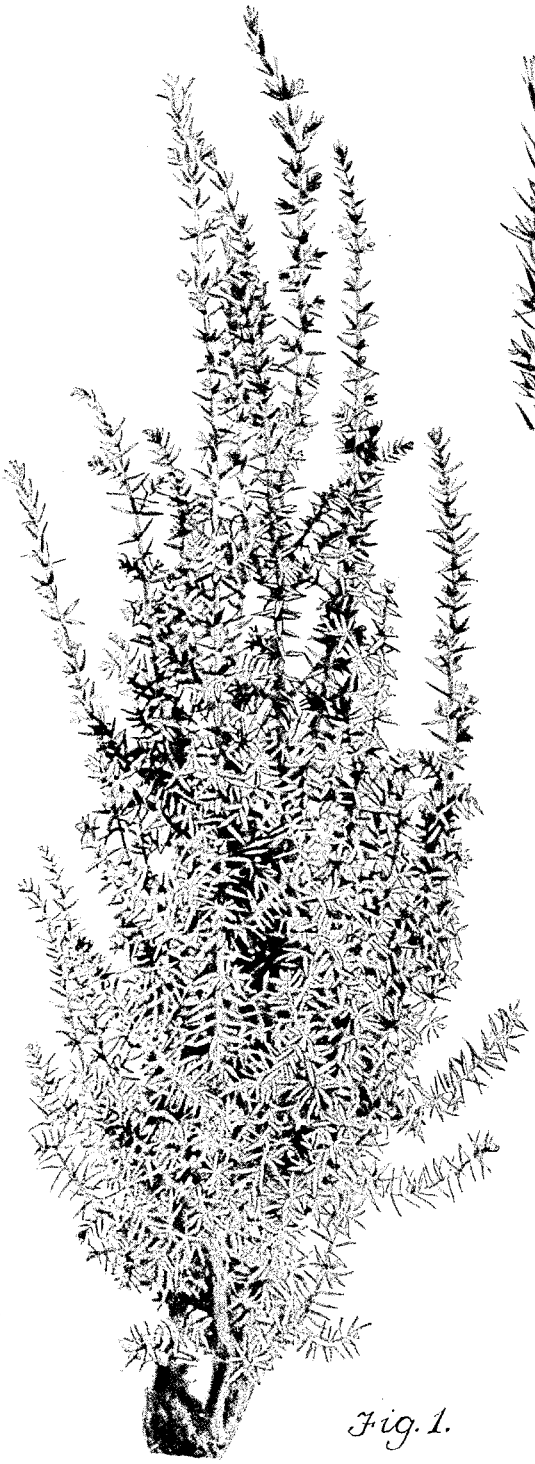
Figure 2:
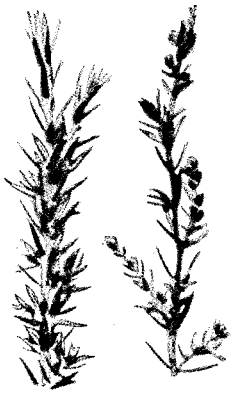
Figure 2 shows, at the left, in natural size, a terminal twig from the specimen depicted in Figure 1, and on the right, a similar twig from a plant of the same age, of the variety *Juniperus hibernica;*
Figure 3:
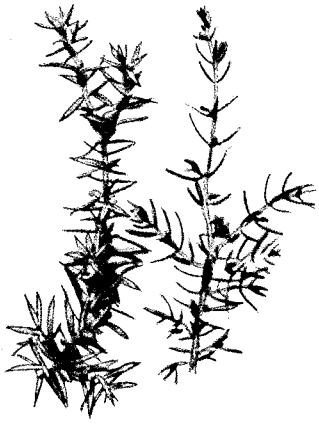
Figure 3 shows, at the left, a more mature twig taken from near the base of the specimen shown in Figure 1, and at the right, a similar twig taken from the base of a three year old specimen of *J. hibernica;*
Figure 4:
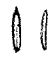
Figure 4 shows, at the left, natural size, an average leaf taken from the new variety, while on the right, it shows a similar leaf taken from *J. hibernica.*

The leaves are dark green beneath, and blue on top. The leaves are distinctly wider than the leaves of *J. suecica* or *J. hibernica.* The average leaf of the new variety measures approximately one-sixteenth of an inch in width, while the average leaf of *J. hibernica* is approximately one-twenty-fourth of an inch, see Figure 4. The relatively wide leaf of the new variety causes the blue color of the top surfaces of the leaves to dominate, in the appearance of the plant as a whole, as shown in Figure 1.

The new variety distinguishes specifically from *J. suecica* in being more narrowly up-right in habit of growth, the back of the leaves being a dark green, while the top surfaces of the leaves are bluer than the blue-white of *suecica*, the leaves being wider and much stiffer. It distinguishes from *hibernica* in the leaves being darker green beneath, bluer on top, set more nearly at right angles to the branches, and being stiffer and therefore more prickly.

The plant originated as a seedling, most probably of *J. communis* and has been perpetuated by common methods of propagation, such as slipping or grafting, as practiced with respect to conifers, so that at the present time several thousand specimens have been propagated, all being true to the original seedling in the above described characteristics.

It is believed that in view of the distinct color and habit of growth of this variety, it represents a valuable addition to the known list of ornamental evergreens.

What I claim is:

The evergreen as described and shown characterized by being narrowly up-right, the leaves wide and stiff, set nearly at right angles to the branches, dark green beneath, blue on top, the width of the leaves accentuating the color appearance of the whole plant and their stiffness and approximately perpendicular relation to the branches giving the plant the characteristic of prickliness.

WILLIS RUSSELL GRAY.